(12) United States Patent
Kim et al.

(10) Patent No.: US 11,145,821 B2
(45) Date of Patent: Oct. 12, 2021

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventors: Seulong Kim, Cheonan-si (KR); Daeyup Shin, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 394 days.

(21) Appl. No.: 16/298,026

(22) Filed: Mar. 11, 2019

(65) Prior Publication Data

US 2019/0288216 A1 Sep. 19, 2019

(30) Foreign Application Priority Data

Mar. 16, 2018 (KR) .................. 10-2018-0030956

(51) Int. Cl.
 *C07D 213/06* (2006.01)
 *C07B 59/00* (2006.01)
 (Continued)

(52) U.S. Cl.
 CPC ........ *H01L 51/0067* (2013.01); *C07B 59/002* (2013.01); *C07D 213/06* (2013.01);
 (Continued)

(58) Field of Classification Search
 CPC ............... C07D 213/06; C07B 59/002; H01L 51/0052; H01L 51/0067; H01L 51/5016
 See application file for complete search history.

(56) References Cited

U.S. PATENT DOCUMENTS

| | | | |
|---|---|---|---|
| 7,833,632 B2 | 11/2010 | Kawamura et al. | |
| 2014/0061594 A1 | 3/2014 | Forrest et al. | |
| 2016/0079543 A1 | 3/2016 | Park et al. | |

FOREIGN PATENT DOCUMENTS

| | | | | |
|---|---|---|---|---|
| CN | 103579528 A | * | 3/2016 | ............. H01L 51/50 |
| JP | 5807601 B2 | | 11/2015 | |

(Continued)

OTHER PUBLICATIONS

SciFinder search (Year: 2021).*
(Continued)

*Primary Examiner* — Vu A Nguyen
(74) *Attorney, Agent, or Firm* — Lewis Roca Rothgerber Christie LLP

(57) ABSTRACT

An organic electroluminescence device includes a first electrode, a hole transport region provided on the first electrode, an emission layer provided on the hole transport region, an electron transport region provided on the emission layer, and a second electrode provided on the electron transport region, wherein the emission layer includes a polycyclic compound represented by Formula 1. In Formula 1, $L_{11}$ and $L_{21}$ are each independently represented by Formula 2, and $L_{12}$ and $L_{22}$ are each independently represented by Formula 3.

Formula 1

Formula 2

(Continued)

-continued

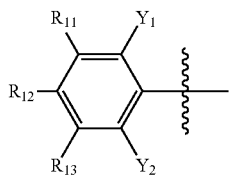

Formula 3

20 Claims, 2 Drawing Sheets

(51) Int. Cl.
*H01L 51/00* (2006.01)
*H01L 51/50* (2006.01)

(52) U.S. Cl.
CPC ...... *H01L 51/0052* (2013.01); *H01L 51/5016* (2013.01); *C07B 2200/05* (2013.01)

(56) References Cited

FOREIGN PATENT DOCUMENTS

| KR | 10-1192512 | B1 | 10/2012 |
| KR | 10-2014-0121388 | A | 10/2014 |
| KR | 10-2016-0031651 | A | 3/2016 |
| KR | 10-1853130 | B1 | 4/2018 |

OTHER PUBLICATIONS

Chiang, Chien-Jung et al.; "Ultrahigh Efficiency Fluorescent Single and Bi-Layer Organic Light Emitting Diodes: The Key Role of Triplet Fusion"; Advanced Functional Materials; 2013; 23; pp. 739-746.

Kondakov, D. Y. et al.; "Triplet annihilation exceeding spin statistical limit in highly efficient fluorescent organic light-emitting diodes"; Journal of Applied Physics; 2009; 106;12; 124510; 8pp.

\* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2018-0030956, filed on Mar. 16, 2018, the entire contents of which are incorporated herein by reference.

BACKGROUND

1. Field

Embodiments of the present disclosure relate to an organic electroluminescence device and a polycyclic compound used for the organic electroluminescence device.

2. Description of the Related Art

The development of an organic electroluminescence display device as an image display device is being actively conducted. Differing from a liquid crystal display device, organic electroluminescence display devices are self-luminescent display devices in which holes and electrons injected from a first electrode and a second electrode recombine in an emission layer, and a light-emitting material which is an organic compound included in the emission layer emits light to display an image.

As an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer has been used. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state. In addition, an embodiment of the configuration of the organic electroluminescence device is not limited thereto, but various modifications may be possible.

SUMMARY

Embodiments of the present disclosure provide an organic electroluminescence device and a polycyclic compound used therein.

An organic electroluminescence device according to an embodiment of the present disclosure includes a first electrode, a hole transport region provided on the first electrode, an emission layer provided on the hole transport region, an electron transport region provided on the emission layer, and a second electrode provided on the electron transport region, wherein the emission layer includes a polycyclic compound represented by Formula 1:

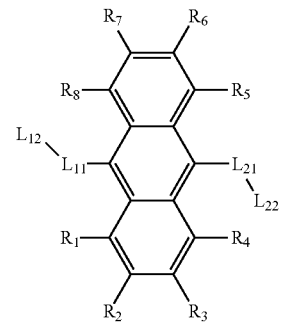

Formula 1

In Formula 1, $R_1$ to $R_8$ are each independently a hydrogen atom or a deuterium atom, $L_{11}$ and $L_{21}$ are each independently represented by Formula 2, and $L_{12}$ and $L_{22}$ are each independently represented by Formula 3:

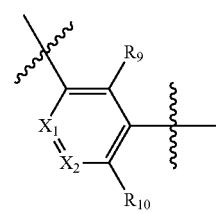

Formula 2

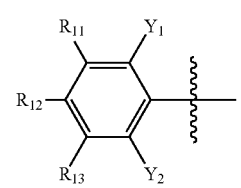

Formula 3

In Formula 2, one of $X_1$ and $X_2$ is CH, and the other one is N. In Formula 3, $Y_1$ and $Y_2$ are each independently a substituted or unsubstituted alkyl group having 1 to 10 carbon atoms. In Formulae 2 and 3, $R_9$ to $R_{13}$ are each independently a hydrogen atom or a deuterium atom.

In an embodiment, a twist angle of a single bond connecting Formula 1 and Formula 2 may be about 60 degrees or more.

In an embodiment, a twist angle of a single bond connecting Formula 2 and Formula 3 may be about 60 degrees or more.

In an embodiment, in Formula 1, each of a chemical structure represented by -$L_{11}$-$L_{12}$ and a chemical structure represented by -$L_{21}$-$L_{22}$ may have the lowest triplet energy level of about 3.3 eV.

In an embodiment, in Formula 3, $Y_1$ and $Y_2$ may be each independently a substituted or unsubstituted methyl group.

In an embodiment, Formula 1 may be represented by Formula 1-1 or Formula 1-2:

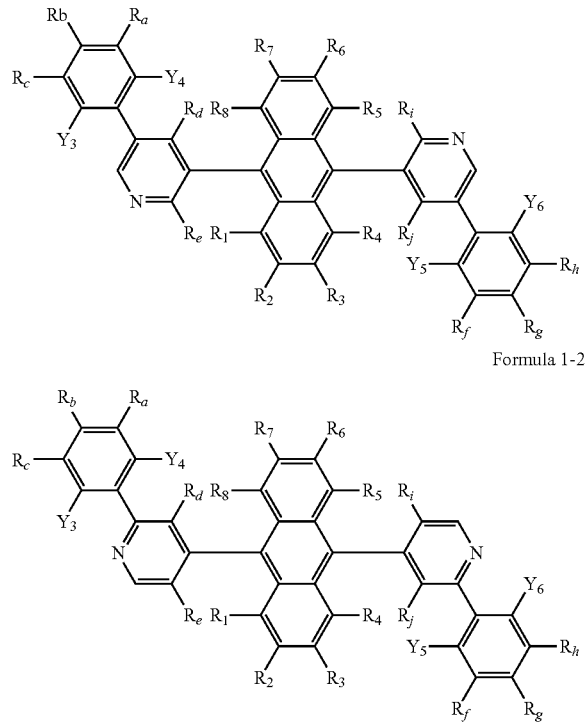

Formula 1-1

Formula 1-2

In Formulae 1-1 and 1-2, $Y_3$ to $Y_6$ are each independently a substituted or unsubstituted alkyl group having 1 to 10 carbon atoms, Ra to $R_j$ are each independently a hydrogen atom or a deuterium atom, and $R_1$ to $R_8$ are the same as defined in Formula 1.

In an embodiment, the emission layer may include a host and a dopant, and the host may include the polycyclic compound represented by Formula 1.

In an embodiment, the emission layer may include a host and a dopant, and the dopant may include the polycyclic compound represented by Formula 1.

In an embodiment, the emission layer may be a blue emission layer which emits blue light.

In an embodiment, the polycyclic compound represented by Formula 1 may satisfy Equation 1:

$$E_{S1} < 2E_{T1} < E_{T2}$$ Equation 1

In Equation 1, $E_{S1}$ is the lowest singlet energy level of the polycyclic compound, $E_{T1}$ is the lowest triplet energy level of the polycyclic compound, and $E_{T2}$ is a second triplet energy level of the polycyclic compound.

An embodiment of the present disclosure provides a polycyclic compound represented by Formula 1 above.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the present disclosure. In the drawings.

DETAILED DESCRIPTION

Figure 1:
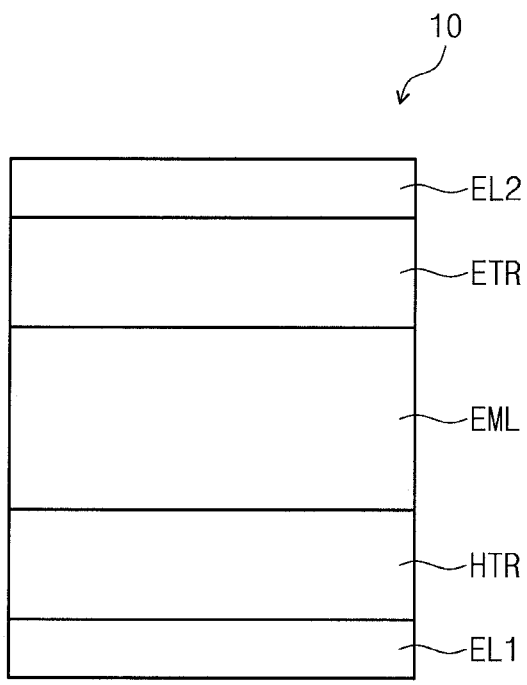
FIG. 1 is a cross-sectional view schematically illustrating an organic electroluminescence device according to an embodiment of the present disclosure.

The above objects, other objects, and features of embodiments of the present disclosure will be easily understood from exemplary embodiments with reference to the accompanying drawings. The subject matter of the present disclosure may, however, be embodied in different forms and should not be construed as limited to the embodiments set forth herein. Rather, exemplary embodiments are provided so that the contents described herein are thorough and complete, and the spirit of the present disclosure is sufficiently understandable for a person skilled in the art.

Like reference numerals refer to like elements throughout each drawing. In the drawings, the sizes of elements may be enlarged for clarity of the present disclosure.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. Additionally, when a layer, a film, a region, a plate, etc. is referred to as being "under" another part, it can be "directly under" the other part, or intervening layers may also be present.

First, organic electroluminescence devices according to exemplary embodiments of the present disclosure will be explained referring to FIG. 1 and FIG. 2.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure.

Figure 2:
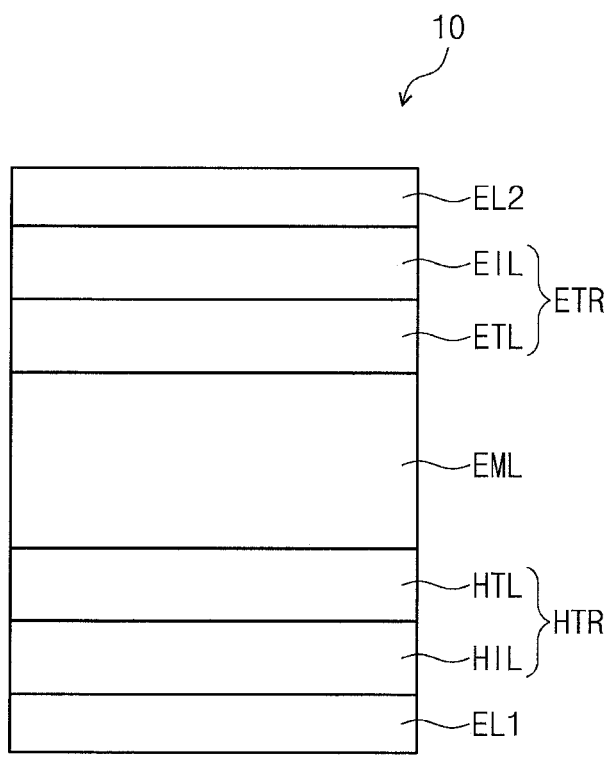
FIG. 2 is a cross-sectional view schematically illustrating an organic electroluminescence device according to an embodiment of the present disclosure.

Referring to FIG. 1 and FIG. 2, an organic electroluminescence device 10 according to an embodiment of the present disclosure includes a first electrode EL1, a hole transport region HTR, an emission layer EML, an electron transport region ETR and a second electrode EL2.

The first electrode EL1 and the second electrode EL2 are oppositely disposed from each other, and a plurality of organic layers may be disposed between the first electrode EL1 and the second electrode EL2. The plurality of the organic layers may include the hole transport region HTR, the emission layer EML, and the electron transport region ETR.

The first electrode EL1 is conductive. The first electrode EL1 may be a pixel electrode or an anode. The first electrode. EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, and/or ITZO. For example, the first electrode EL1 may have a triple layer structure of ITO/Ag/ITO, without limitation.

The thickness of the first electrode EL1 may be about 1,000 Å to about 10,000 Å, for example, about 1,000 Å to about 3,000 Å.

The hole transport region HTR is provided on the first electrode EL1. The hole transport region HTR may include at least one of a hole injection layer HIL, a hole transport layer HTL, a hole buffer layer, and/or an electron blocking layer. The thickness of the hole transport region HTR may be, for example, about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, and may have a single layer structure formed using a hole injection material and a hole transport material. In some embodiments, the hole transport region HTR may have a single layer structure formed using a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various suitable methods such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino) triphenylamine (m-MTDATA), 4,4', 4''-tris(N,N-diphenylamino)triphenylamine (TDATA), 4,4', 4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris (N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. If the hole transport region HTR includes both hole injection layer HIL and hole, transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, suitable or satisfactory hole transport properties may be obtained without a substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of a quinone derivative, a metal oxide, and/or a cyano group-containing compound, without limitation. For example, non-limiting examples of the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide, and molybdenum oxide, without limitation.

As described above, the hole transport region HTR may further include at least one of a hole buffer layer and/or an electron blocking layer in addition to the hole injection layer HIL and the hole transport layer HTL. The hole buffer layer may compensate for a resonance distance according to the wavelength of light emitted from the emission layer EML and increase light emission efficiency. Materials included in the hole transport region HTR may be used as materials included in the hole buffer layer. The electron blocking layer is a layer that prevents or reduces electron injection from the electron transport region ETR to the hole transport region HTR.

The emission layer EML is provided on the hole transport region HTR. The emission layer EML may have a thickness of, for example, about 100 Å to about 1,000 Å, or about 100 Å to about 300 Å. The emission layer EML may have a single layer formed using a single material, a single layer formed using a plurality of different materials, or a multilayer structure having a plurality of layers formed using a plurality of different materials.

The materials and emission wavelength of the emission layer EML will be explained in more detail herein below.

The electron transport region ETR is provided on the emission layer EML. The electron transport region ETR may include at least one of a hole blocking layer, an electron transport layer ETL, and/or an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. Further, the electron transport region ETR may have a single layer structure having a plurality of different materials, or a structure laminated from the emission layer EML of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various suitable methods such as a vacuum deposition method, a spin coating method, a cast method, a Langmuir-Blodgett (LB) method, an inkjet printing method, a laser printing method, and/or a laser induced thermal imaging (LITI) method.

If the electron transport region ETR includes an electron transport layer ETL, the electron transport region ETR may include an anthracene-based compound. However, an embodiment of the present disclosure is not limited thereto. The electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate) ($Bebq_2$), 9,10-di(naphthalene-2-yl)anthracene (ADN), or a mixture thereof. The thickness of the electron transport layer ETL may be from about 100 Å to about 1,000 Å, for example, from about 150 Å to about 500 Å. If the thickness of the electron transport layer ETL satisfies the above-described range, suitable or satisfactory electron transport properties may be obtained without a substantial increase of a driving voltage.

If the electron transport region ETR includes an electron injection layer EIL, the electron transport region ETR may use LiF, lithium quinolate (LiQ), $Li_2O$, BaO, NaCl, CsF, a metal in lanthanides such as Yb, and/or a metal halide such as RbCl, and RbI. However, an embodiment of the present disclosure is not limited thereto. The electron injection layer EIL may also be formed using a mixture material of an electron transport material and an insulating organo metal salt. The organo metal salt may be a material having an energy band gap of about 4 eV or more. In some embodiments, the organo metal salt may include, for example, a metal acetate, a metal benzoate, a metal acetoacetate, a metal acetylacetonate, and/or a metal stearate. The thickness of the electron injection layer EIL may be from about 1 Å to about 100 Å, from about 3 Å to about 90 Å. If the thickness of the electron injection layer EIL satisfies the above-described range, suitable or satisfactory electron injection properties may be obtained without a substantial increase of a driving voltage.

The electron transport region ETR may include a hole blocking layer as described above. The hole blocking layer may include, for example, 2,9-dimethyl-4,7-diphenyl-1,10-phenanthroline (BCP), and/or 4,7-diphenyl-1,10-phenanthroline (Bphen). However, an embodiment of the present disclosure is not limited thereto.

The second electrode EL2 is provided on the electron transport region ETR. The second electrode EL2 may be a common electrode or a cathode. The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light via a transition from an excited state to a ground state.

If the organic electroluminescence device 10 is a top emission type (or kind), the first electrode EL1 may be a reflective electrode and the second electrode EL2 may be a transmissive electrode or a transflective electrode. If the organic electroluminescence device 10 is a bottom emission type (or kind), the first electrode EL1 may be a transmissive electrode or a transflective electrode and the second electrode EL2 may be a reflective electrode.

An embodiment of the present disclosure provides a polycyclic compound for an organic electroluminescence device. An emission layer EML includes the polycyclic compound according to an embodiment of the present disclosure. For example, the polycyclic compound according to an embodiment of the present disclosure may be used as a material for an emission layer EML of an organic electroluminescence device 10.

Hereinafter, the polycyclic compound according to an embodiment of the present disclosure will be explained in more detail.

As used herein, the symbol

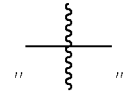

refers to a part to be connected.

As used herein, the term "substituted or unsubstituted" may mean substituted with at least one substituent selected from the group consisting of a deuterium atom, a halogen group, a cyano group, a nitro group, an amino group, a silyl group, a boron group, a phosphine oxide group, a phosphine sulfide group, an alkyl group, an alkenyl group, an aryl group, and a heterocycle, or unsubstituted. In addition, each of the substituents described herein above may be substituted or unsubstituted. For example, a biphenyl group may be interpreted as an aryl group or a phenyl group substituted with a phenyl group. The heterocyclic group includes an aliphatic heterocycle and an aromatic heterocycle (heteroaryl group).

For example, as used herein, the term "substituted or unsubstituted" may mean substituted or unsubstituted with one or more substituents selected from the group consisting of a deuterium atom, a halogen atom, an alkyl group, and an aryl group.

In the present disclosure, examples of the halogen atom may include a fluorine atom, a chlorine atom, a bromine atom and an iodine atom.

In the present disclosure, an alkyl group may be a linear, branched or cyclic type (or kind) of alkyl group. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, an alkenyl group may be a linear chain or a branched chain alkenyl group. The carbon number is not specifically limited but may be 2 to 30, 2 to 20, or 2 to 10. Examples of the alkenyl group include vinyl, 1-butenyl, 1-pentenyl, 1,3-butadienyl aryl, styrenyl, styrylvinyl, etc., without limitation.

As used herein, the term "aryl group" means an optional functional group or substituent derived from an aromatic hydrocarbon ring. The aryl group may be a monocyclic aryl or a polycyclic aryl. The carbon number for forming a ring in the aryl group may be 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the description, a fluorenyl group may be substituted, and two substituents may be combined with each other to form a Spiro structure. Examples of a substituted fluorenyl group are shown herein below. However, an embodiment of the present disclosure is not limited thereto.

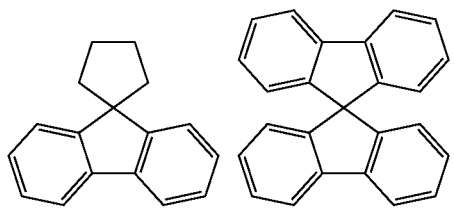

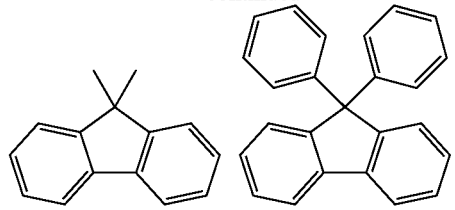

In the present disclosure, a heteroaryl group may be a heteroaryl group including at least one of O, N, P, Si or S as a heteroatom.

In the present disclosure, a silyl group includes an alkyl silyl group and an aryl silyl group. Examples of the silyl may include trimethylsilyl, triethylsilyl, t-butyldimethylsilyl, vinyldimethylsilyl, propyldimethylsilyl, triphenylsilyl, diphenylsilyl, phenylsilyl, etc. However, an embodiment of the present disclosure is not limited thereto.

In the present disclosure, a boron group includes an alkyl boron group and an aryl boron group. Examples of the boron group include trimethylboron, triethylboron, t-butyldimethylboron, triphenylboron, diphenylboron, phenylboron, etc., without limitation.

In the present disclosure, a carbon number of an amino group is not specifically limited, but may be 1 to 30. The amino group may include an alkyl amino group and an aryl amino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the present disclosure, a phosphine oxide group may be substituted with, for example, at least one of an alkyl group or an aryl group. Examples of the phosphine oxide group may include a phenyl phosphine oxide group, a diphenyl phosphine oxide group, etc., without limitation.

In the present disclosure, a phosphine sulfide group may be substituted with, for example, at least one of an alkyl group or an aryl group.

The polycyclic compound according to an embodiment of the present disclosure is represented by Formula 1:

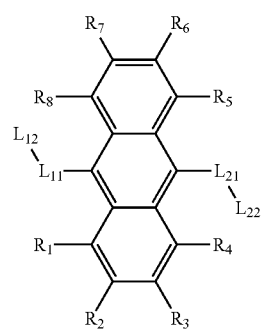

Formula 1

In Formula 1, $R_1$ to $R_8$ are each independently a hydrogen atom, or a deuterium atom.

In Formula 1, $L_{11}$ and $L_{21}$ are each independently represented by Formula 2:

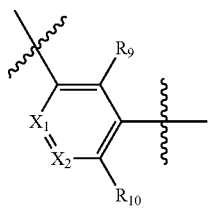

Formula 2

In Formula 2, one of $X_1$ and $X_2$ is CH and the other one is N, and $R_9$ and $R_{10}$ are each independently a hydrogen atom or a deuterium atom.

In Formula 1, $L_{12}$ and $L_{22}$ are each independently represented by Formula 3:

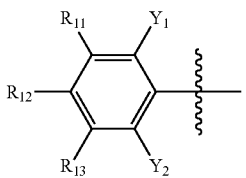

Formula 3

In Formula 3, $Y_1$ and $Y_2$ are each independently a substituted or unsubstituted alkyl group having 1 to 10 carbon atoms, and $R_{11}$ to $R_{13}$ are each independently a hydrogen atom or a deuterium atom.

In Formula 1, $L_{11}$ and $L_{21}$ may be the same. However, an embodiment of the present disclosure is not limited thereto.

In Formula 1, $L_{12}$ and $L_{22}$ may be the same. However, an embodiment of the present disclosure is not limited thereto.

In Formula 1, each of $R_1$ to $R_9$ may be a hydrogen atom. However, an embodiment of the present disclosure is not limited thereto, and at least one of $R_1$ to $R_8$ may be a deuterium atom.

In Formula 2, each of $R_9$ and $R_{10}$ may be a hydrogen atom. However, an embodiment of the present disclosure is not limited thereto, and at least one of $R_9$ or $R_{10}$ may be a deuterium atom.

In Formula 3, $Y_1$ and $Y_2$ may be each independently a substituted or unsubstituted methyl group. For example, each of $Y_1$ and $Y_2$ may be a methyl group.

Formula 1 may be, for example, represented by Formula 1-1:

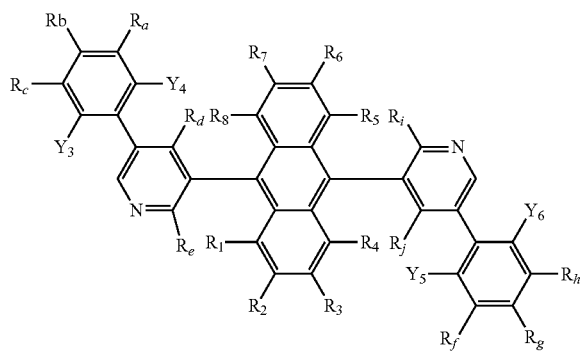

Formula 1-1

In Formulae 1-1, $Y_3$ to $Y_6$ are each independently a substituted or unsubstituted alkyl group having 1 to 10 carbon atoms, Ra to $R_j$ are each independently a hydrogen atom or a deuterium atom, and $R_1$ to $R_8$ are the same as defined in Formula 1.

Formula 1-1 may be represented, for example, by Formula 1-1-1:

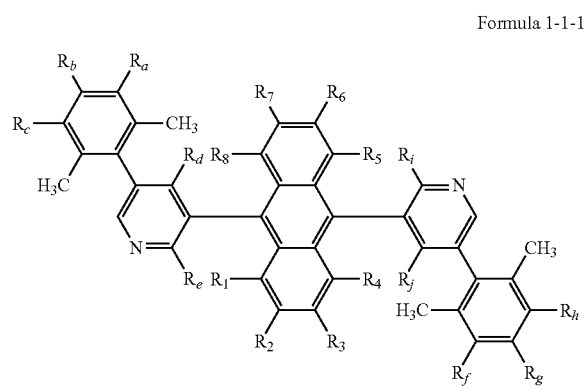

Formula 1-1-1

In Formula 1-1-1, Ra to $R_j$, and $R_1$ to $R_8$ are each independently a hydrogen atom or a deuterium atom.

In another embodiment, Formula 1 may be represented by Formula 1-2:

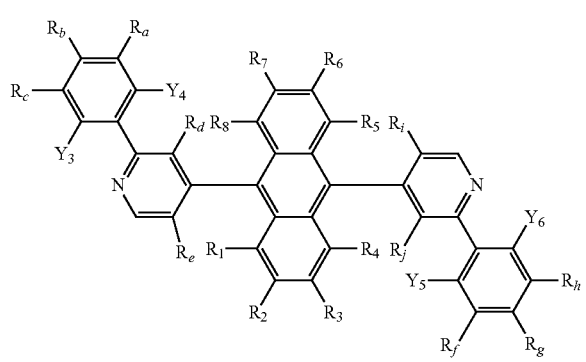

Formula 1-2

In Formula 1-2, $Y_3$ to $Y_6$ are each independently a substituted or unsubstituted alkyl group having 1 to 10 carbon atoms, Ra to $R_j$ are each independently a hydrogen atom or a deuterium atom, and $R_1$ to $R_8$ are the same as defined in Formula 1.

Formula 1 may be represented, for example, by Formula 1-2-1:

Formula 1-2-1

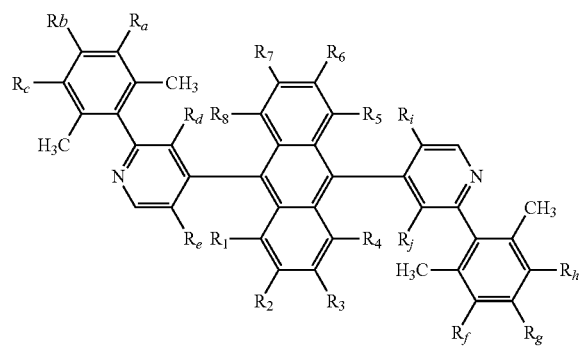

In Formula 1-2-1, Ra to Rj, and R1 to R8 are each independently a hydrogen atom or a deuterium atom.

The polycyclic compound represented by Formula 1 according to an embodiment of the present disclosure may be any one selected from the compounds represented in Compound Group 1. However, an embodiment of the present disclosure is not limited thereto.

Compound Group 1

1

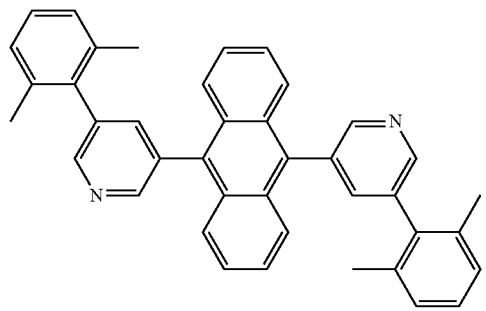

2

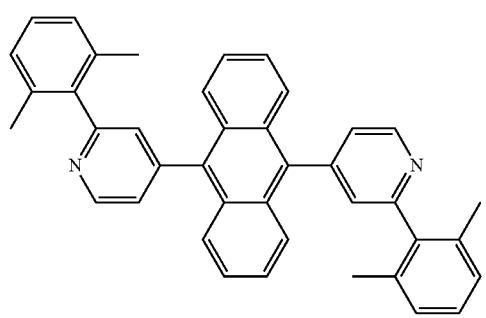

3

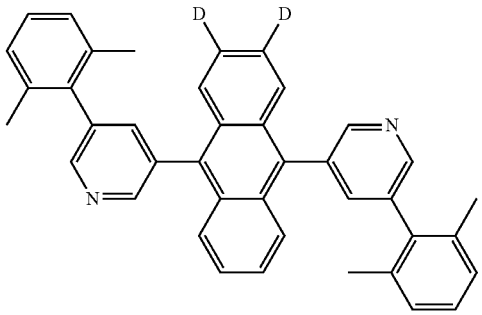

4

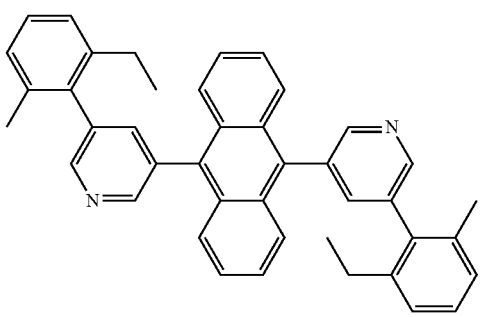

5

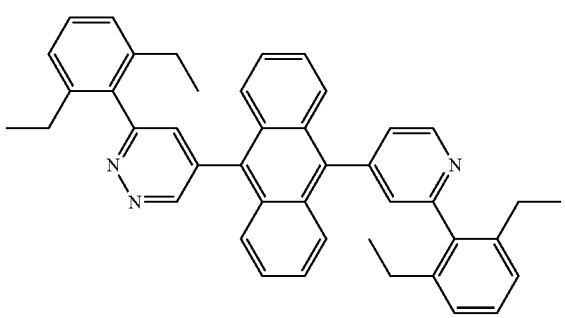

6

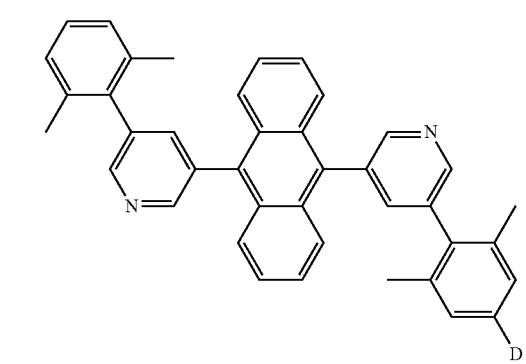

7

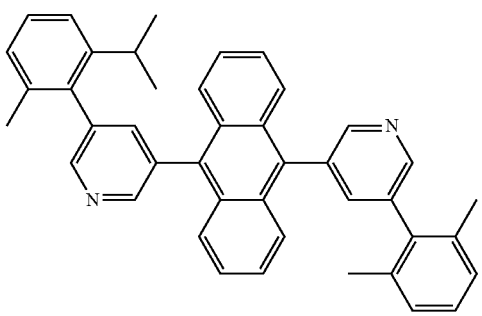

-continued

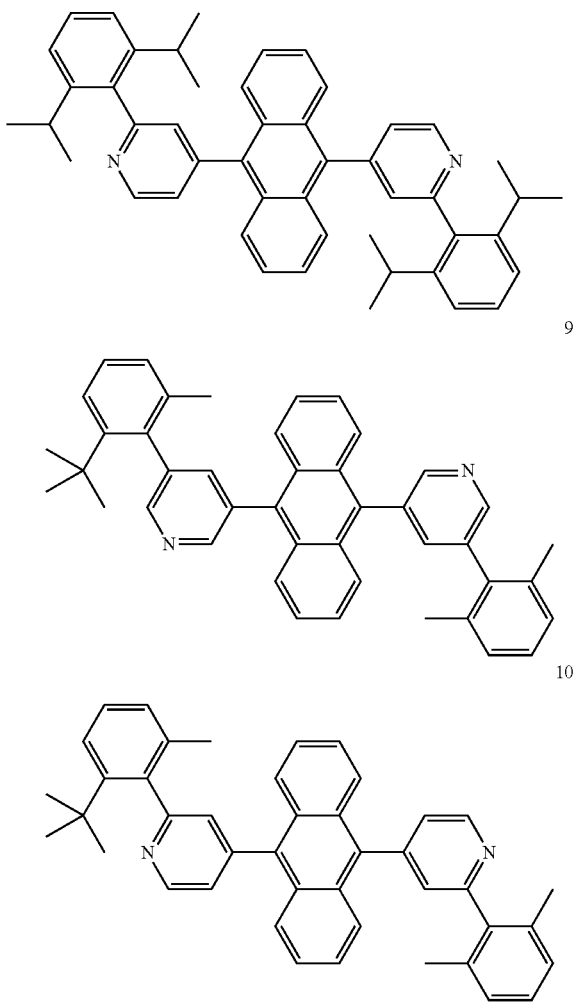

The polycyclic compound according to an embodiment of the present disclosure has a structure in which the anthracene group of Formula 1 is a core structure and ligands are introduced at positions 9 and 10 of the anthracene group, respectively. The ligands have a chemical structure represented by -L$_{11}$-L$_{12}$ or a chemical structure represented by -L$_{21}$-L$_{22}$. In Formula 1, each of the chemical structures represented by -L$_{11}$-L$_{12}$ and -L$_{21}$-L$_{22}$ has the lowest triplet energy level of about 3.3 eV or more.

The polycyclic compound according to an embodiment of the present disclosure includes a ligand having a relatively high lowest triplet energy level in a core structure to increase the second triplet energy of the whole molecule. Accordingly, a relation of 2E$_{T1}$<E$_{T2}$ may be satisfied.

Figure 3:
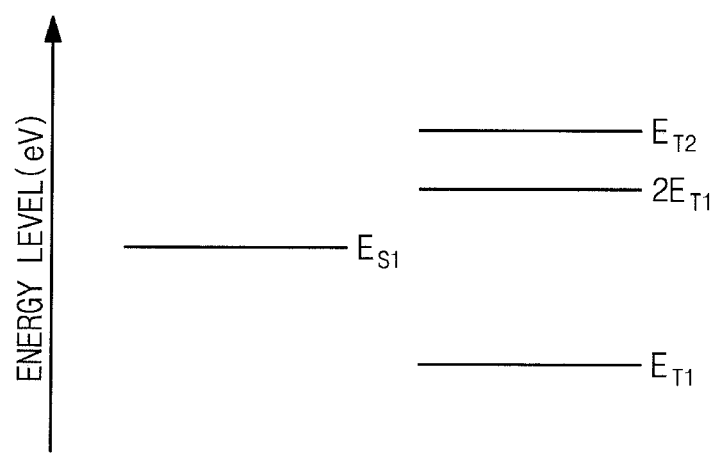
FIG. 3 is an energy diagram of a polycyclic compound according to an embodiment of the present disclosure.

FIG. 3 is an energy diagram of a polycyclic compound according to an embodiment of the present disclosure.

Referring to FIG. 3, the polycyclic compound represented by Formula 1 according to an embodiment of the present disclosure may satisfy Equation 1:

$$E_{S1} < 2E_{T1} < E_{T2} \quad \text{Equation 1}$$

In Equation 1, E$_{S1}$ is the lowest singlet energy level (the first singlet energy level) of the polycyclic compound, E$_{T1}$ is the lowest triplet energy level (the first triplet energy level) of the polycyclic compound, and E$_{T2}$ is the second triplet energy level of the polycyclic compound.

If Equation 1 is satisfied and a triplet-triplet fusion (TTA) phenomenon occurs, an energy transition to the second triplet state does not arise (or does not substantially arise), and instead an energy transition to the lowest singlet energy state (the first singlet energy state) occurs. Accordingly, maximally about 50% of the triplet excitation state may transit (or transition) to a singlet excitation state, and the inner quantum efficiency of an organic electroluminescence device may become maximally about 62.5%. For example, if the polycyclic compound according to an embodiment of the present disclosure is applied to an organic electroluminescence device, the inner quantum efficiency of the organic electroluminescence device may be from about 40% to about 62.5%.

The twist angle of a single bond connecting Formula 1 and Formula 2 may be about 60 degrees or more. In other words, the twist angle of a single bond connecting a core structure and a ligand may be about 60 degrees or more. Accordingly, conditions for generating energy conversion may be attained only in the core structure (e.g., may substantially be confined to the core structure), and energy loss may be minimized or reduced. As a result, if such a compound is applied to an organic electroluminescence device, high efficiency may be achieved.

In the present disclosure, "twist angle" may mean a twisted angle of two cores in a plane structure. For example, the "twist angle" may be defined as the angle between a plane that is parallel to the width of the anthracene ring of Formula 1 and a plane that is parallel to the width of the ring of Formula 2, and/or the "twist angle" may be defined as the angle between a plane that is parallel to the width of the ring of Formula 2 and a plane that is parallel to the width of the ring of Formula 3. "Twist angle" may be, for example, a calculated value by using the Gaussian 09 program using density functional theory (DFT) and the B3LYP functional and the 6-31G* basis set (e.g., DFT B3LYP/6-31G*).

The twist angle of a single bond connecting Formula 2 and Formula 3 may be about 60 degrees or more. According to the twist angle of the chemical structure represented by Formula 2 and the chemical structure represented by Formula 3 of about 60 degrees or more, the breakage of conjugation and the decrease of the lowest triplet energy level may be prevented or reduced. In order to accomplish the twist angle of about 60 degrees or more, a substituent may be introduced to each of Y$_1$ and Y$_2$ of Formula 3, and for example, Y$_1$ and Y$_2$ may each independently be a substituted or unsubstituted alkyl group having 1 to 10 carbon atoms.

Formula 2 and Formula 3 are connected at a meta position (e.g., Formula 3 may be bonded to Formula 2 at a meta position of Formula 2, based on the bonding of Formula 2 to the anthracene group of Formula 1), and thus, if applied to an organic electroluminescence device, excellent layer forming properties may be achieved. For example, if Formula 2 and Formula 3 are connected at the para position (e.g., Formula 3 may be bonded to Formula 2 at the para position of Formula 2, based on the bonding of Formula 2 to the anthracene group of Formula 1), due to the increased interaction between molecules, molecular stacking may be promoted, crystallization may be easily generated, and an opaque layer may be formed.

In Formula 2, a part represented by Q1 may be connected with Formula 1 and a part represented by Q2 may be connected with Formula 3.

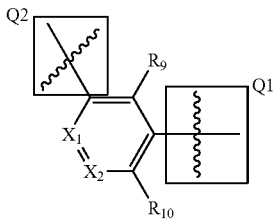

The nitrogen atom (N) of Formula 2 may be positioned at a meta or para position relative to the anthracene of Formula 1. If the nitrogen atom (N) of Formula 2 is positioned at an ortho position relative to the anthracene of Formula 1, the relation of $2E_{T1}<E_{T2}$ may not be satisfied.

Referring to FIGS. 1-2 again, an emission layer EML included in the organic electroluminescence device 10 according to an embodiment of the present disclosure will be explained in more detail.

As described above, the emission layer EML includes the polycyclic compound according to an embodiment of the present disclosure. In some embodiments, the emission layer EML includes the polycyclic compound represented by Formula 1. The emission layer EML may include one or two or more kinds of the polycyclic compound according to an embodiment of the present disclosure.

The emission layer EML may include a host and a dopant. The host may include the polycyclic compound according to an embodiment of the present disclosure, and the dopant may be a blue dopant. However, an embodiment of the present disclosure is not limited thereto. The dopant may include the polycyclic compound according to an embodiment of the present disclosure.

The emission layer EML may further include any suitable material available in the art in addition to the polycyclic compound according to an embodiment of the present disclosure. As the host material, any suitable host materials available in the art may be used without limitation. For example, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TcTa), and/or 1,3,5-tris(N-phenylbenzimidazol-2-yl)benzene (TPBi) may be included. However, an embodiment of the present disclosure is not limited thereto and may use, for example, tris(8-hydroxyquinolino)aluminum (Alq$_3$), 4,4'-bis(N-carbazolyl)-1,1'-biphenyl (CBP), poly(N-vinylcarbazole) (PVK), 9,10-di (naphthalene-2-yl)anthracene (ADN), 4,4',4''-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), 2,8-bis(diphenylphosphoryl)dibenzofuran (PPF), etc. as a host material.

For example, the emission layer EML may further include at least one of 4,4'-bis(2-(9-ethyl-9H-carbazol-3-yl)vinyl)-1,1'-biphenyl; 4,4'-bis(9-ethyl-3-carbazolvinylene)-1,1'-biphenyl (BCzVBi), 10-phenyl-10H,10'H-spiro[acridine-9,9'-anthracene]-10'-one (ACRSA), 3,4,5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-9,9-dimethyl-9,10-dihydroacridine)phenyl]sulfone (DMAC-DPS), and/or 2-phenoxazine-4,6-diphenyl-1,3,5-triazine (PSZ-TRZ). In addition, as the dopant material of the emission layer EML, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and/or 1,4-bis(N,N-diphenylamino) pyrene), may be further included.

The emission layer EML may be a blue emission layer capable of emitting blue light. The emission layer EML may be an emission layer capable of emitting light having a wavelength region of about 510 nm or less, or about 480 nm or less. The emission layer EML may be a fluorescence emission layer capable of fluorescence.

The organic electroluminescence device according to an embodiment of the present disclosure uses the polycyclic compound according to an embodiment of the present disclosure, and thus, efficiency may be improved.

Hereinafter, the present disclosure will be explained in more detail with reference to examples and comparative examples. However, the following examples are only illustrations to assist the understanding of the subject matter of the present disclosure, and the scope of the present disclosure is not limited thereto.

Synthetic Examples

The polycyclic compound according to an embodiment of the present disclosure may be synthesized, for example, as follows. However, the synthetic method of the polycyclic compound according to an embodiment of the present disclosure is not limited thereto.

1. Synthesis of Compound 1

Compound 1 according to an embodiment of the present disclosure may be synthesized, for example, as follows.

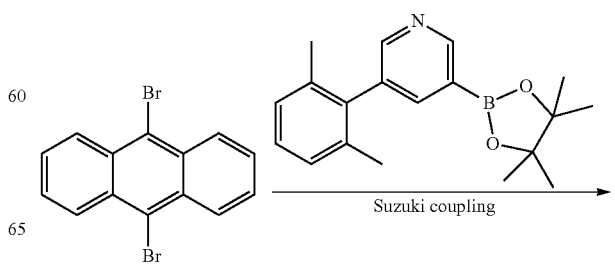

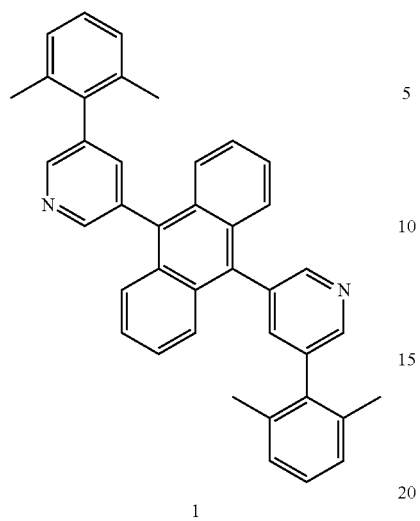

1

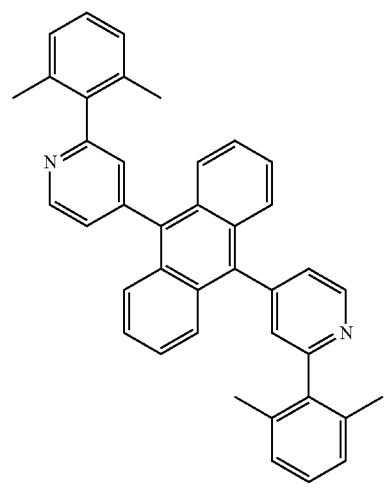

2

3 g (0.0089 mol) of 9,10-dibromoanthracene and 5.51 g (0.0178 mol) of 3-(2,6-dimethylphenyl)-5-(4,4,5,5-tetramethyl-1,3,2-dioxaborolan-2-yl)pyridine were added to a 3-neck flask (100 ml), and then, 3 ml of 2 N Na$_2$CO$_3$ and a mixture solution of toluene/EtOH were added thereto, followed by stirring while removing oxygen. After that, the inside of the flask was substituted with nitrogen and 0.5 g of a Pd(pph$_3$)$_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA): hexane (1:5) to obtain 3.85 g (80% yield) of Compound 1.

[H-NMR (CDCl$_3$): 9.34 (4H, s), 8.43 (2H, d), 8.20 (4H, d), 7.53-7.28 (6H, m), 7.23 (4H, d), 2.58 (12H, s)]

3 g (0.0089 mol) of 9,10-dibromoanthracene and 5.51 g (0.0178 mol) of 2-(2,6-dimethylphenyl)-4-(4,4,5,5-tetramethyl-1,3,2-dioxaborolan-2-yl)pyridine were added to a 3-neck flask (100 ml), and then, 3 ml of 2 N Na$_2$CO$_3$ and a mixture solution of toluene/EtOH were added thereto, followed by stirring while removing oxygen. After that, the inside of the flask was substituted with nitrogen and 0.5 g of a Pd(pph$_3$)$_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA): hexane (1:5) to obtain 3.75 g (78% yield) of Compound 2.

[H-NMR (CDCl$_3$): 8.56 (4H, m), 8.21 (4H, d), 8.01 (2H, d), 7.53-7.28 (6H, m), 7.23 (4H, d), 2.58 (12H, s)]

2. Synthesis of Compound 2

Compound 2 according to an embodiment of the present disclosure may be synthesized, for example, as follows.

3. Synthesis of Compound T-1

Compound T-1 according to an embodiment of the present disclosure may be synthesized, for example, as follows.

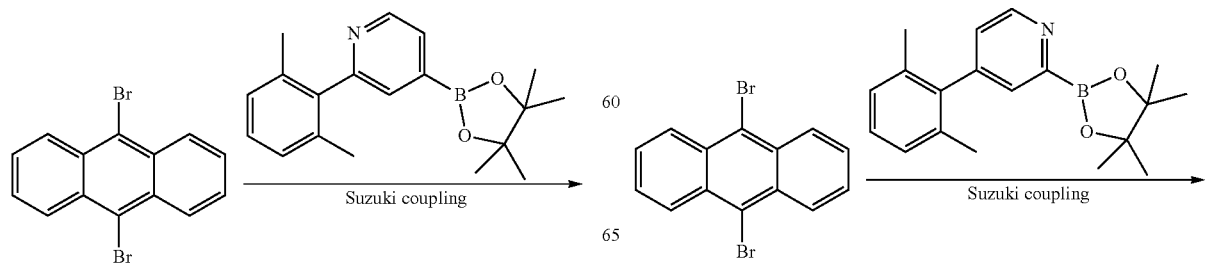

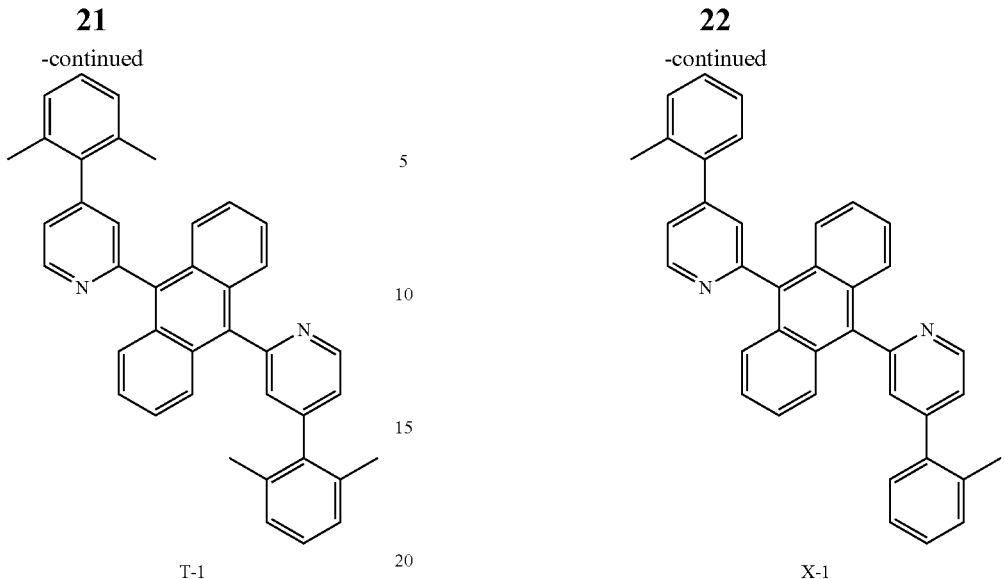

T-1

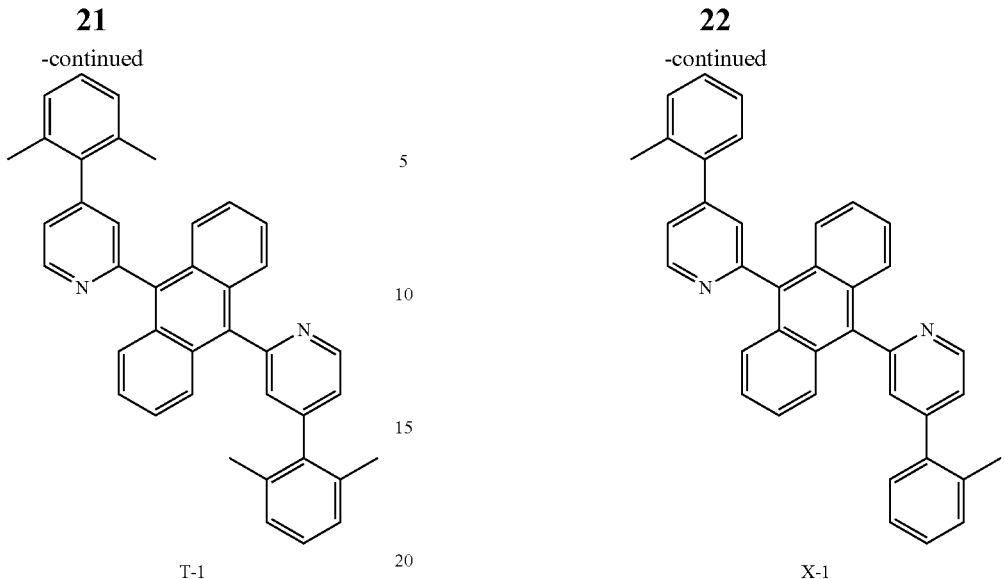

X-1

3 g (0.0089 mol) of 9,10-dibromoanthracene and 5.51 g (0.0178 mol) of 4-(2,6-dimethylphenyl)-2-(4,4,5,5-tetramethyl-1,3,2-dioxaborolan-2-yl)pyridine were added to a 3-neck flask (100 ml), and then, 3 ml of 2 N(Normality) Na$_2$CO$_3$ and a mixture solution of toluene/EtOH were added thereto, followed by stirring while removing oxygen. After that, the inside of the flask was substituted with nitrogen and 0.5 g of a Pd(pph$_3$)$_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA):hexane (1:5) to obtain 3.75 g (78% yield) of Compound T-1.

[H-NMR (CDCl$_3$): 8.58 (4H, d), 8.21 (4H, d), 8.01 (2H, d), 7.50-7.28 (6H, m), 7.22 (4H, d), 2.58 (12H, s)]

The above-described synthetic examples are exemplary embodiments and reaction conditions may be changed as necessary or desired.

For comparative experimental examples, Comparative Compounds X-1 to X-3 were synthesized as follows.

4. Synthesis of Comparative Compound X-1

3 g (0.0089 mol) of 9,10-dibromoanthracene and 5.26 g (0.0178 mol) of 2-(4,4,5,5-tetramethyl-1,3,2-dioxaborolan-2-yl)-4-(o-tolyl)pyridine were added to a 3-neck flask (100 ml), and then, 3 ml of 2 N Na$_2$CO$_3$ and a mixture solution of toluene/EtOH were added thereto, followed by stirring while removing oxygen. After that, the inside of the flask was substituted with nitrogen and 0.5 g of a Pd(pph$_3$)$_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA):hexane (1:5) to obtain 3.89 g (85% yield) of Comparative Compound X-1.

[H-NMR (CDCl$_3$): 8.56 (4H, m), 8.21 (4H, d), 8.01 (2H, d), 7.72 (2H, d), 7.47-7.30 (10H, m), 2.23 (6H, s)]

5. Synthesis of Comparative Compound X-2

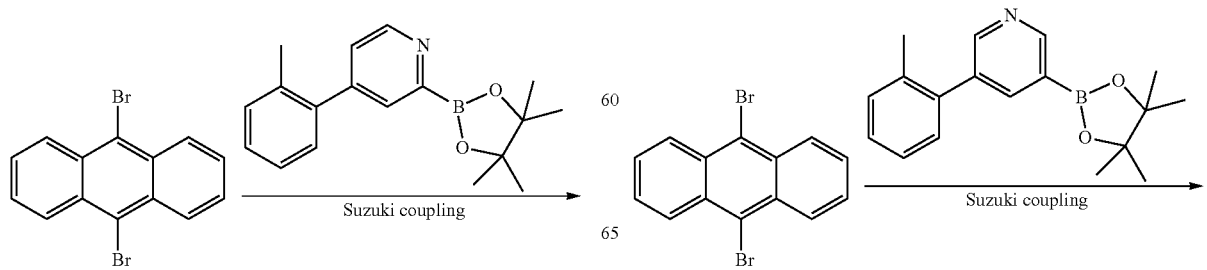

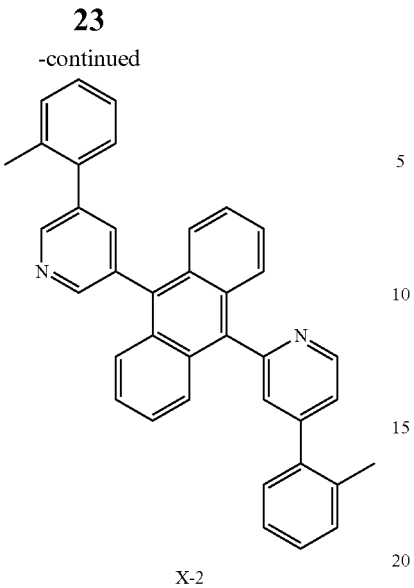

X-2

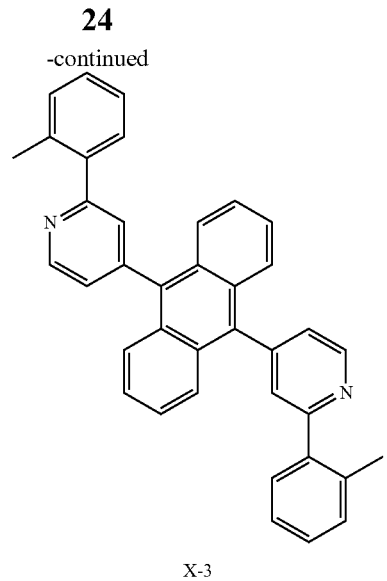

X-3

3 g (0.0089 mol) of 9,10-dibromoanthracene and 5.26 g (0.0178 mol) of 3-(4,4,5,5-tetramethyl-1,3,2-dioxaborolan-2-yl)-5-(o-tolyl)pyridine were added to a 3-neck flask (100 ml), and then, 3 ml of 2 N $Na_2CO_3$ and a mixture solution of toluene/EtOH were added thereto, followed by stirring while removing oxygen. After that, the inside of the flask was substituted with nitrogen and 0.5 g of a $Pd(pph_3)_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA):hexane (1:5) to obtain 3.89 g (85% yield) of Comparative Compound X-2.

[H-NMR ($CDCl_3$): 9.34 (4H, s), 8.43 (2H, s), 8.21 (4H, d), 7.72 (2H, d), 7.47-7.30 (10H, m), 2.23 (6H, s)]

6. Synthesis of Comparative Compound X-3

3 g (0.0089 mol) of 9,10-dibromoanthracene and 5.26 g (0.0178 mol) of 4-(4,4,5,5-tetramethyl-1,3,2-dioxaborolan-2-yl)-2-(o-tolyl)pyridine were added to a 3-neck flask (100 ml), and then, 3 ml of 2 N $Na_2CO_3$ and a mixture solution of toluene/EtOH were added thereto, followed by stirring while removing oxygen. After that, the inside of the flask was substituted with nitrogen and 0.5 g of a $Pd(pph_3)_4$ catalyst was added, followed by refluxing at about 110° C. for about 8 hours. The reaction was quenched using water, the reaction product was extracted with methylene chloride (MC) three times, and the solvents were removed. The resultant product was separated by column chromatography using a solvent of ethyl acetate (EA):hexane (1:5) to obtain 3.65 g (80% yield) of Comparative Compound X-3.

[H-NMR ($CDCl_3$): 8.56 (4H, m), 8.21 (4H, d), 8.01-7.98 (4H, m), 7.47 (4H, t), 7.35-7.27 (6H, m), 2.23 (6H, s)]

The results of $E_{S1}$, $E_{T1}$ and $E_{T2}$ of Example Compounds 1, 2 and T-1 and Comparative Compounds X-1 to X-3 calculated using the B3LYP functional and 6-31G basis set (B3LYP/6-31G) using the Gaussian '09 software program are shown in Table 1 below. In addition, the measured results of the twist angle of a single bond of a structure corresponding to Formula 2 and a structure corresponding to Formula 3 in each compound are shown in Table 1 below.

TABLE 1

|  | $E_{S1}$ (eV) | $E_{T1}$ (eV) | $E_{T2}$ (eV) | Twist angle (°) |
|---|---|---|---|---|
| Example Compound 1 | 3.07 | 1.65 | 3.41 | 65 |
| Example Compound 2 | 3.09 | 1.66 | 3.43 | 65 |
| Example Compound T-1 | 3.09 | 1.66 | 3.20 | 65 |
| Comparative Compound X-1 | 3.09 | 1.66 | 3.21 | 58 |
| Comparative Compound X-2 | 3.07 | 1.65 | 3.24 | 58 |
| Comparative Compound X-3 | 3.09 | 1.66 | 3.28 | 58 |

(Device manufacturing examples) Organic electroluminescence devices of exemplary embodiments were manufactured using Compounds 1, 2 and T-1 as the host materials of an emission layer.

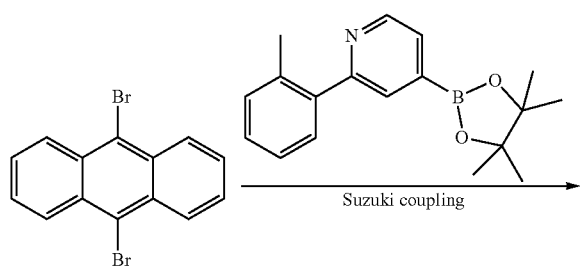

Example Compounds
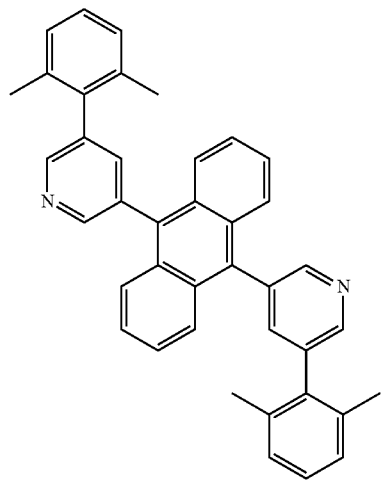
1
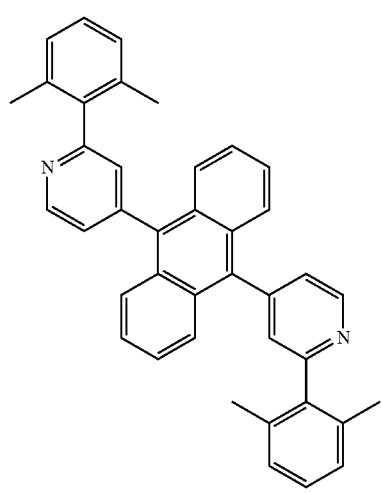
2
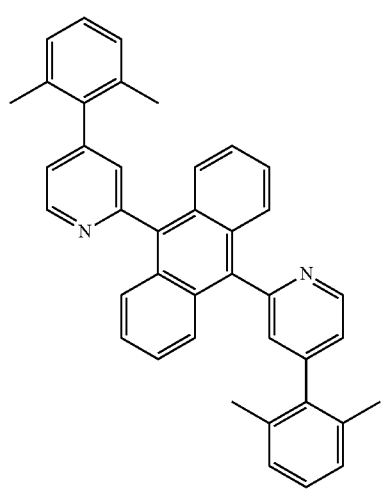
T-1
Comparative Compounds
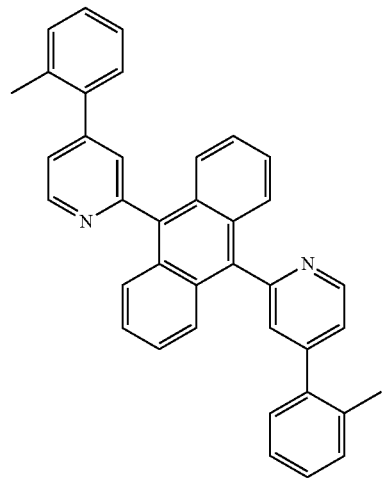
X-1
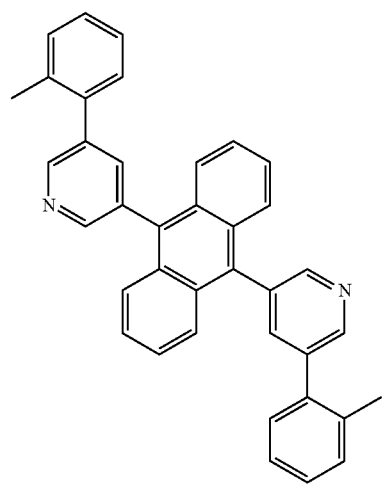
X-2
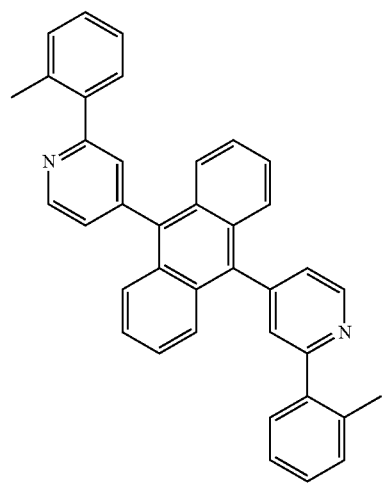
X-3
Organic electroluminescence devices of comparative examples were manufactured using Comparative Compounds X-1 to X-3 and an existing material, mADN, as the host materials of an emission layer.

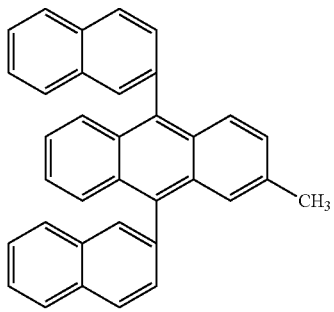
mADN

The organic electroluminescence devices of the examples and the comparative examples were manufactured as follows.

An ITO glass substrate was cut to a size of 50 mm×50 mm×0.5 mm and ultrasonically cleaned using isopropyl alcohol and pure water for about 10 minutes, respectively. The ITO glass substrate was cleaned by irradiating ultraviolet rays and exposing to ozone for about 10 minutes, and then was installed in a vacuum deposition apparatus. On the ITO glass substrate, an existing hole transport material was deposited in vacuum to form a hole transport region. On the hole transport region, one of the example compounds or the comparative compounds was co-deposited with a BCzVBi dopant to form an emission layer. Then, on the emission layer, an existing electron transport material was deposited in vacuum to form an electron transport region, and Al was deposited to form a second electrode.

The emission efficiency, the life and the retardant fluorescence ratio of the organic electroluminescence devices according to the examples and the comparative examples were measured and are shown in Table 2 below.

TABLE 2

| Emission layer host material | Dopant ratio | Emission efficiency (cd/A) | Life (LT 90) | Retardant fluorescence ratio (%) |
|---|---|---|---|---|
| Example 1 | Compound 1 | 3% | 10.5 | 58 | 58 |
| Example 2 | Compound 1 | 5% | 10.8 | 60 | 59 |
| Example 3 | Compound 2 | 3% | 11.2 | 49 | 49 |
| Example 4 | Compound 2 | 5% | 11.5 | 55 | 52 |
| Example 5 | Compound T-1 | 3% | 7.2 | 32 | 28 |
| Example 6 | Compound T-1 | 5% | 7.5 | 55 | 29 |
| Comparative Example 1 | Compound X-1 | 3% | 7.3 | 50 | 28 |
| Comparative Example 2 | Compound X-1 | 5% | 7.0 | 52 | 29 |
| Comparative Example 3 | Compound X-2 | 3% | 6.8 | 58 | 30 |
| Comparative Example 4 | Compound X-2 | 5% | 6.9 | 60 | 31 |
| Comparative Example 5 | Compound X-3 | 3% | 5.2 | 46 | 30 |
| Comparative Example 6 | Compound X-3 | 5% | 5.9 | 49 | 30 |
| Comparative Example 7 | mADN | 5% | 6.5 | 5 | 23 |

The resultant values are measured values at a luminance of about 1,000 cd/m². Referring to the results of Table 2 above, Examples 1 to 4 used Compound 1 or 2 as the host of an emission layer and were found to have better efficiency and longer life than Comparative Examples 1 to 7.

More particularly, Compounds 1 and 2 correspond to Formula 3 where each of $Y_1$ and $Y_2$ is a methyl group, while, Comparative Compounds X-1 to X-3 correspond to Formula 3 where one of $Y_1$ and $Y_2$ is a methyl group and the other one is a hydrogen atom. As shown in the results of Table 1, Comparative Compounds X-1 to X-3 have a twist angle of Formula 2 and Formula 3 of less than 60 degrees, and conjugation is insufficiently broken and the second triplet energy of a whole molecule becomes relatively decreased. As a result, Comparative Examples 1 to 6 using Comparative Compounds X-1 to X-3 have relatively decreased delayed fluorescence ratios, which are also shown in Table 2 above.

As shown in the results of Table 1, Example Compounds 1 and 2 satisfied the above Equation 1, and delayed fluorescence ratios were high, which are also shown in Table 2 above.

Meanwhile, Examples 5 and 6 used Compound T-1 in which a nitrogen atom of Formula 2 is positioned at an ortho position with respect to the anthracene group of Compound 1, as the host material of an emission layer. From the analysis results, the second triplet energy was insufficiently increased when compared to cases having meta or para relation. Accordingly, in some embodiments, the nitrogen atom of Formula 2 and the anthracene group of Formula 1 should satisfy meta or para relation.

The polycyclic compound according to an embodiment of the present disclosure has excellent singlet conversion ratio, and if applied to an organic electroluminescence device, high efficiency may be achieved.

The organic electroluminescence device according to an embodiment of the present disclosure has excellent efficiency.

The polycyclic compound according to an embodiment of the present disclosure is applied to an organic electroluminescence device and contributes to the increase of efficiency.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

As used herein, the term "and/or" includes any and all combinations of one or more of the associated listed items. Expressions such as "at least one of," when preceding a list of elements, modify the entire list of elements and do not modify the individual elements of the list. As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although exemplary embodiments of the present disclosure have been described, it is understood that the present disclosure should not be limited to these exemplary embodiments, but various changes and modifications can be made by one ordinary skilled in the art within the spirit and scope of the present disclosure as hereinafter claimed.

What is claimed is:
1. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the emission layer comprises a polycyclic compound represented by Formula 1:

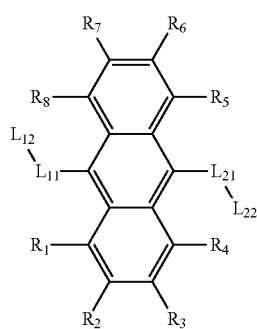

Formula 1 in Formula 1,
$R_1$ to $R_8$ are each independently a hydrogen atom or a deuterium atom,
$L_{11}$ and $L_{21}$ are each independently represented by Formula 2, and
$L_{12}$ and $L_{22}$ are each independently represented by Formula 3:

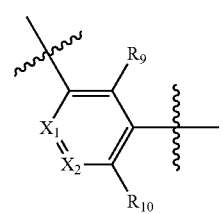

Formula 2

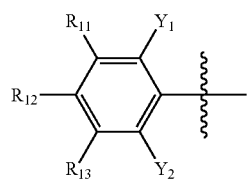

Formula 3 in Formula 2, one of $X_1$ and $X_2$ is CH, and the other one is N, and $R_9$ and $R_{10}$ are each independently a hydrogen atom or a deuterium atom, and in Formula 3, $Y_1$ and $Y_2$ are each independently a substituted or unsubstituted alkyl group having 1 to 10 carbon atoms, and $R_{11}$ to $R_{13}$ are each independently a hydrogen atom or a deuterium atom.

2. The organic electroluminescence device of claim 1, wherein a twist angle of a single bond connecting Formula 1 and Formula 2 is 60 degrees or more.

3. The organic electroluminescence device of claim 2, wherein a twist angle of a single bond connecting Formula 2 and Formula 3 is 60 degrees or more.

4. The organic electroluminescence device of claim 1, wherein in Formula 1, each of a chemical structure represented by $-L_{11}-L_{12}$ and a chemical structure represented by $-L_{21}-L_{22}$ has a lowest triplet energy level of 3.3 eV.

5. The organic electroluminescence device of claim 1, wherein $Y_1$ and $Y_2$ are each independently a substituted or unsubstituted methyl group.

6. The organic electroluminescence device of claim 1, wherein Formula 1 is represented by Formula 1-1:

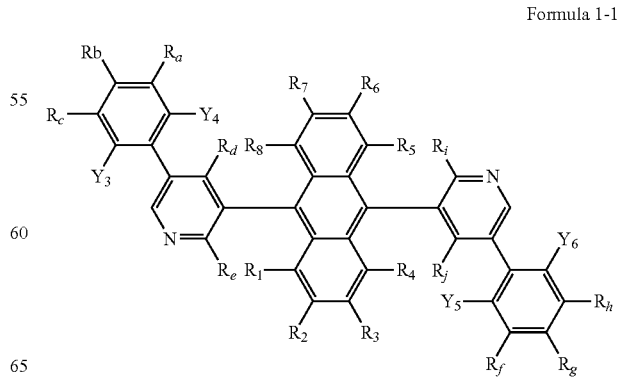

Formula 1-1 in Formula 1-1,

Y$_3$ to Y$_6$ are each independently a substituted or unsubstituted alkyl group having 1 to 10 carbon atoms, Ra to R$_j$ are each independently a hydrogen atom or a deuterium atom, and R$_1$ to R$_8$ are the same as defined in Formula 1.

7. The organic electroluminescence device of claim 1, wherein Formula 1 is represented by Formula 1-2:

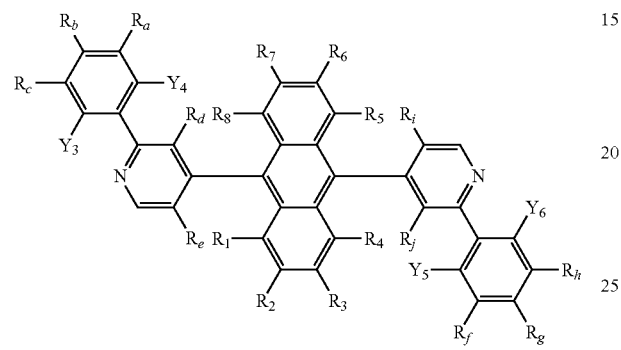

Formula 1-2 in Formula 1-2,

Y$_3$ to Y$_6$ are each independently a substituted or unsubstituted alkyl group having 1 to 10 carbon atoms, Ra to R$_j$ are each independently a hydrogen atom or a deuterium atom, and R$_1$ to R$_8$ are the same as defined in Formula 1.

8. The organic electroluminescence device of claim 1, wherein:

the emission layer comprises a host and a dopant, and the host comprises the polycyclic compound represented by Formula 1.

9. The organic electroluminescence device of claim 1, wherein:

the emission layer comprises a host and a dopant, and the dopant comprises the polycyclic compound represented by Formula 1.

10. The organic electroluminescence device of claim 1, wherein the emission layer is a blue emission layer which emits blue light.

11. The organic electroluminescence device of claim 1, wherein the polycyclic compound represented by Formula 1 satisfies Equation 1:

$$E_{S1} < 2E_{T1} < E_{T2} \qquad \text{Equation 1}$$

in Equation 1, $E_{S1}$ is the lowest singlet energy level of the polycyclic compound, $E_{T1}$ is the lowest triplet energy level of the polycyclic compound, and $E_{T2}$ is the second triplet energy level of the polycyclic compound.

12. The organic electroluminescence device of claim 1, wherein the polycyclic compound represented by Formula 1 is at least one selected from compounds represented in Compound Group 1:

Compound Group 1

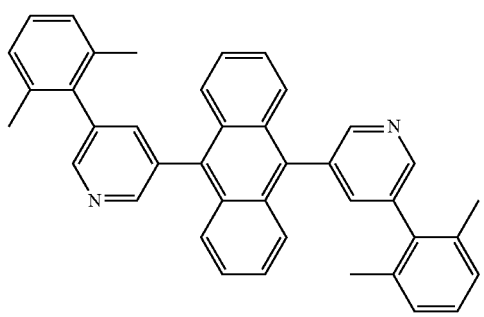

1

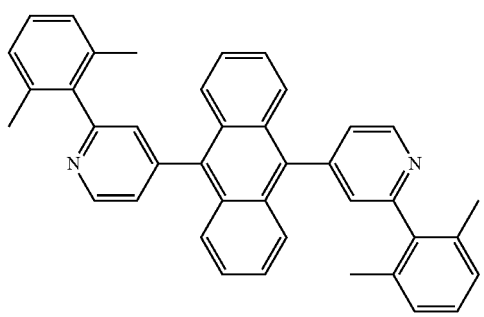

2

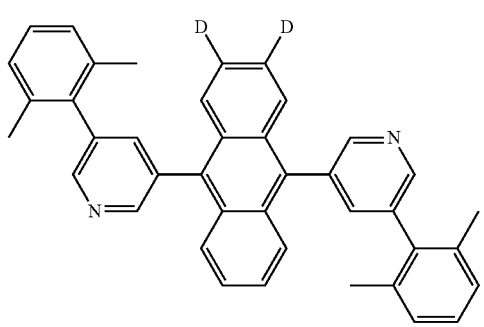

3

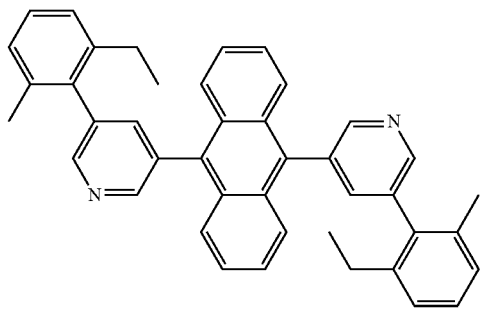

4

5
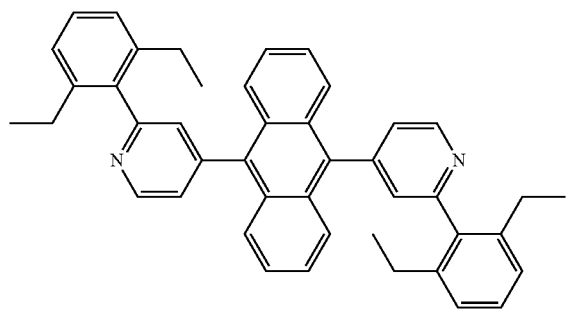
6
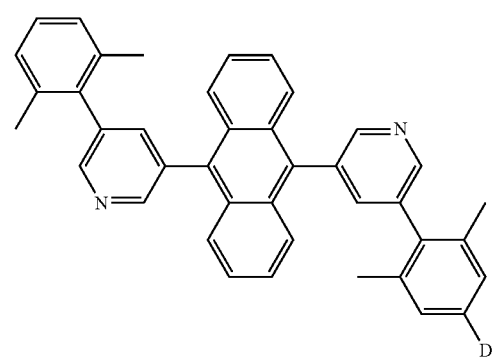
7
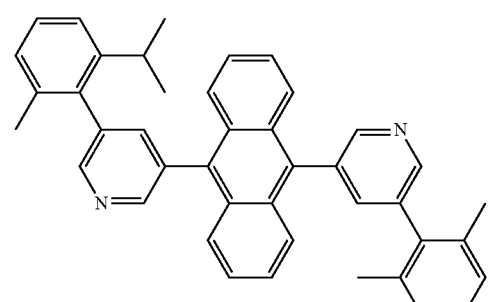
8
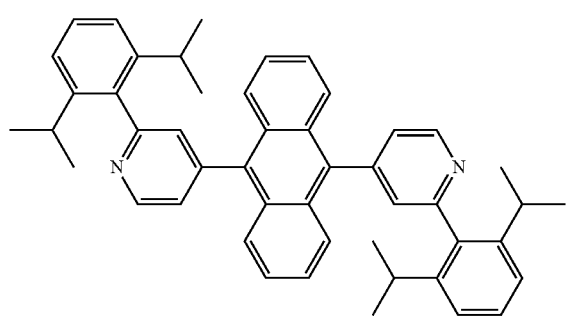
9
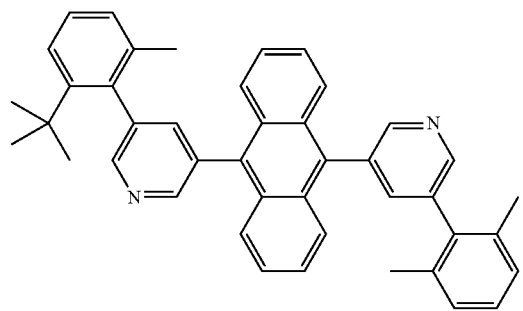
10
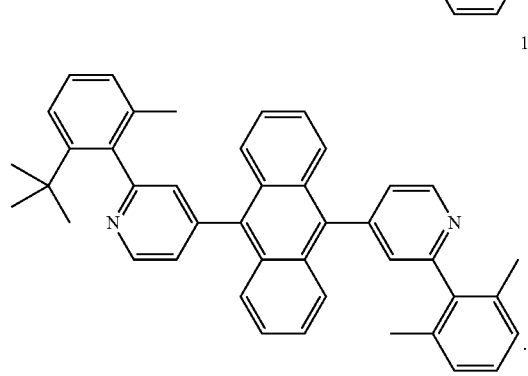
13. A polycyclic compound represented by Formula 1:
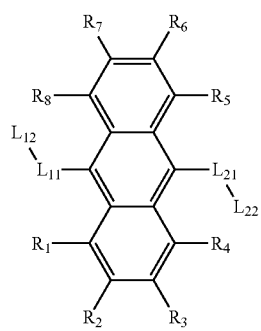
Formula 1
in Formula 1,
R$_1$ to R$_8$ are each independently a hydrogen atom or a deuterium atom,
L$_{11}$ and L$_{21}$ are each independently represented by Formula 2, and
L$_{12}$ and L$_{22}$ are each independently represented by Formula 3:
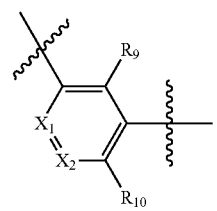
Formula 2

-continued

Formula 3

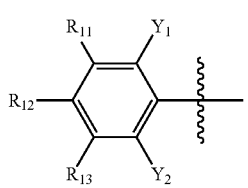

in Formula 2, one of $X_1$ and $X_2$ is CH, and the other one is N, and $R_9$ and $R_{10}$ are each independently a hydrogen atom or a deuterium atom, and in Formula 3, $Y_1$ and $Y_2$ are each independently a substituted or unsubstituted alkyl group having 1 to 10 carbon atoms, and $R_{11}$ to $R_{13}$ are each independently a hydrogen atom or a deuterium atom.

14. The polycyclic compound of claim 13, wherein a twist angle of a single bond connecting Formula 1 and Formula 2 is 60 degrees or more.

15. The polycyclic compound of claim 14, wherein a twist angle of a single bond connecting Formula 2 and Formula 3 is 60 degrees or more.

16. The polycyclic compound of claim 13, wherein in Formula 1, each of a chemical structure represented by -$L_{11}$-$L_{12}$ and a chemical structure represented by -$L_{21}$-$L_{22}$ has a lowest triplet energy level of 3.3 eV.

17. The polycyclic compound of claim 13, wherein $Y_1$ and $Y_2$ are each independently a substituted or unsubstituted methyl group.

18. The polycyclic compound of claim 13, wherein Formula 1 is represented by Formula 1-1 or Formula 1-2:

Formula 1-1

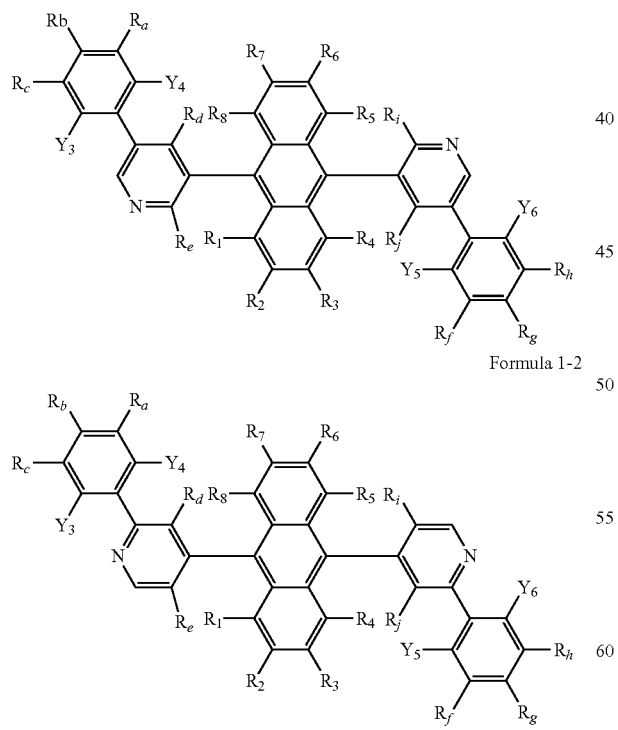

Formula 1-2

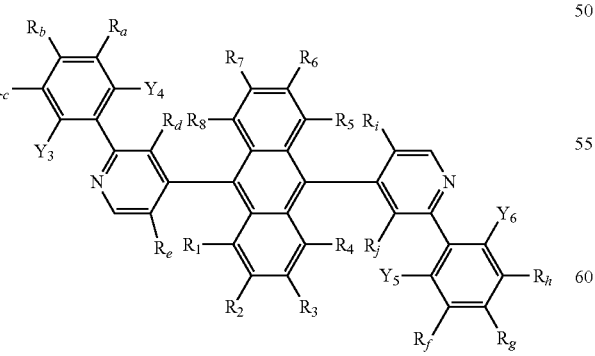

in Formulae 1-1 and 1-2,
$Y_3$ to $Y_6$ are each independently a substituted or unsubstituted alkyl group having 1 to 10 carbon atoms, Ra to $R_j$ are each independently a hydrogen atom or a deuterium atom, and $R_1$ to $R_8$ are the same as defined in Formula 1.

19. The polycyclic compound of claim 13, wherein the polycyclic compound satisfies Equation 1:

$$E_{S1} < 2E_{T1} < E_{T2} \qquad \text{Equation 1}$$

in Equation 1, $E_{S1}$ is the lowest singlet energy level of the polycyclic compound, $E_{T1}$ is the lowest triplet energy level of the polycyclic compound, and $E_{T2}$ is the second triplet energy level of the polycyclic compound.

20. The polycyclic compound of claim 13, wherein the polycyclic compound represented by Formula 1 is at least one selected from compounds represented in Compound Group 1:

Compound Group 1

1

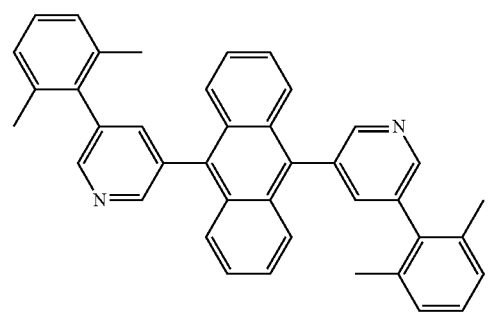

2

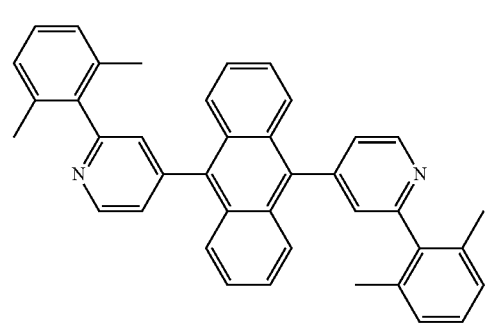

3

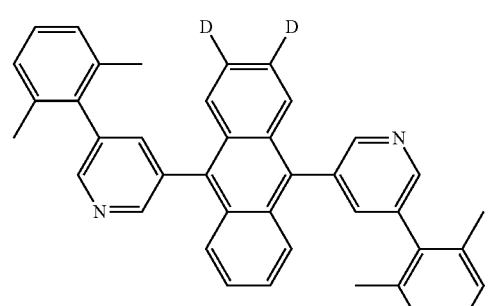

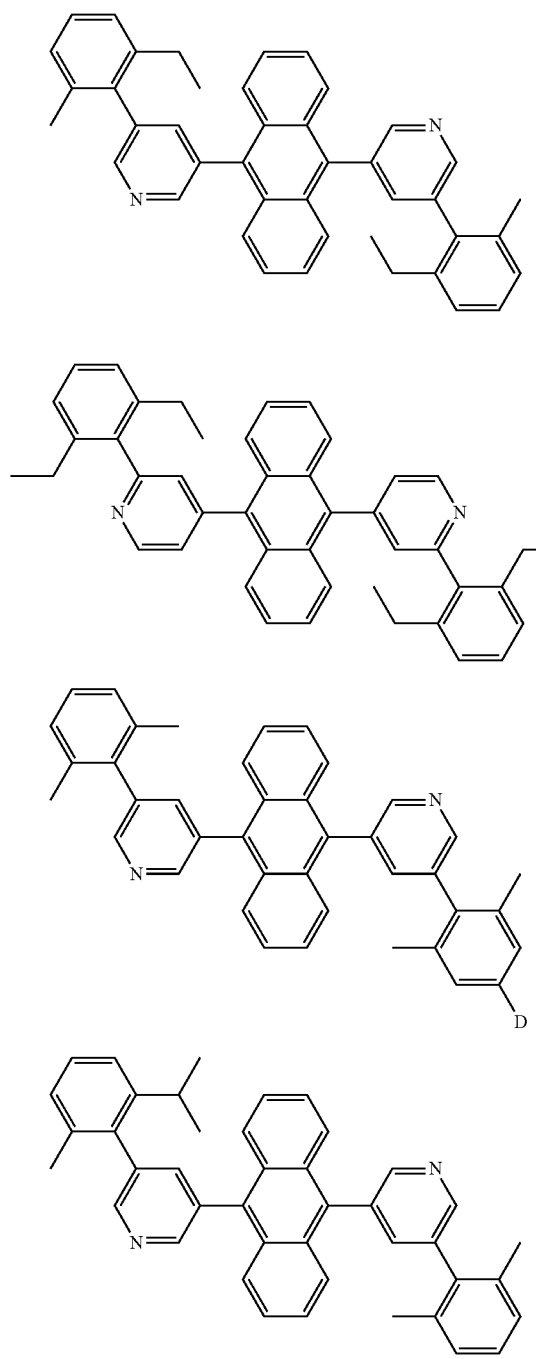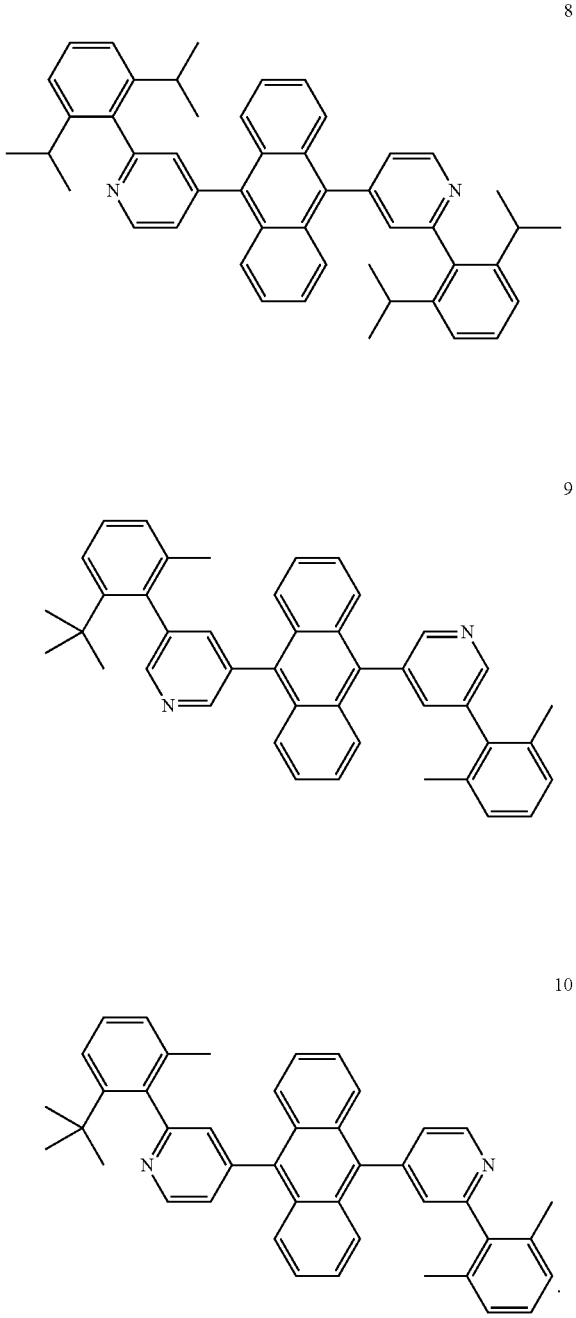
* * * * *